United States Patent [19]
Bettez et al.

[11] Patent Number: 5,693,096
[45] Date of Patent: Dec. 2, 1997

[54] VOCAL CORD MEDIALIZING DEVICE

[76] Inventors: Maurice Bettez; Christian Ahmarani, both of 5900, Boulevard Léger/402, Montreal, Quebec, Canada, H1G 1K9

[21] Appl. No.: 503,550
[22] Filed: Jul. 18, 1995
[51] Int. Cl.⁶ ..................... A61F 2/20
[52] U.S. Cl. ..................... 623/9; 623/11
[58] Field of Search ..................... 623/9, 10, 11, 623/17

[56] References Cited

U.S. PATENT DOCUMENTS

| | | | |
|---|---|---|---|
| 4,892,546 | 1/1990 | Kotz et al. | 623/18 |
| 5,197,982 | 3/1993 | Goldsmith, III et al. | 623/9 |
| 5,306,298 | 4/1994 | Godley, III et al. | 623/9 |
| 5,344,453 | 9/1994 | Montgomery et al. | 623/9 |
| 5,375,823 | 12/1994 | Navas | 623/17 |
| 5,549,673 | 8/1996 | Beale | 623/9 |
| 5,593,439 | 1/1997 | Cummings et al. | 623/9 |

FOREIGN PATENT DOCUMENTS

| | | | |
|---|---|---|---|
| 0453186 | 10/1991 | European Pat. Off. | 623/9 |
| 3729600 | 3/1989 | Germany | 623/17 |
| 9418913 | 9/1994 | WIPO | 623/17 |

*Primary Examiner*—John G. Weiss
*Assistant Examiner*—Bruce E. Snow

[57] ABSTRACT

An adjustable prosthetic device for medializing a paralyzed vocal cord. The device includes a guiding sleeve which defines a channel. The channel is closed at one end thereof by a base wall. The guiding sleeve is configured and sized so as to be insertable in a window formed in the thyroid cartilage of a patient. A biasing block is slidably inserted in the channel. The biasing block is movable between a retracted position wherein the biasing block is in a substantially proximal relationship relatively to the base wall, and a protracted position wherein the biasing block is in a substantially spaced relationship relatively to the base wall. An adjustment screw is provided for moving the biasing block between its protracted and retracted positions. The adjustment screw is rotatably attached to the sleeve base wall and is threadaly attached to the biasing block. A pair of substantially "Y"-shaped anchoring structures extends integrally and substantially outwardly from the opposed end peripheral edges of the base wall. Each anchoring structure includes a substantially annular-shaped main fixing ring and a pair of substantially annular-shaped auxiliary fixing rings. The auxiliary fixing rings are substantially symmetrically disposed relatively to the main fixing ring. The main fixing ring and the auxiliary fixing rings are adapted to receive a corresponding set of anchoring screws for fixing the device on the thyroid cartilage of the patient.

18 Claims, 3 Drawing Sheets

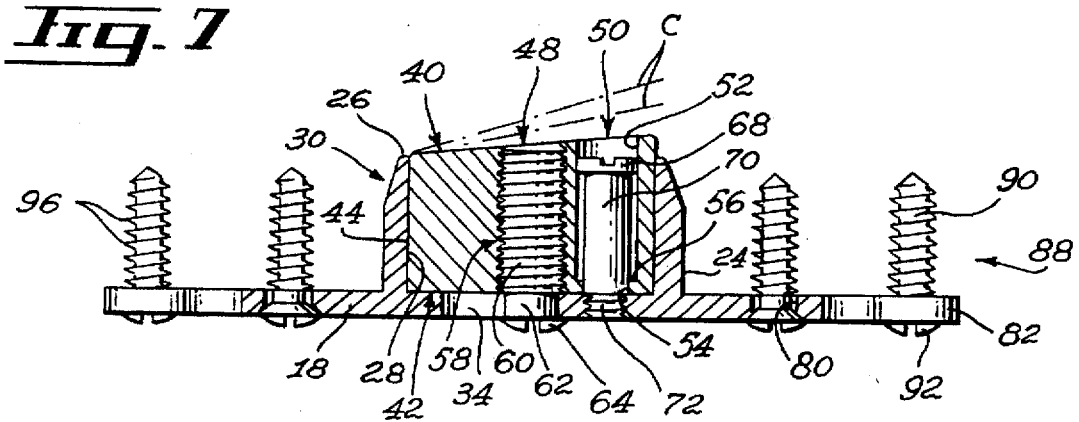
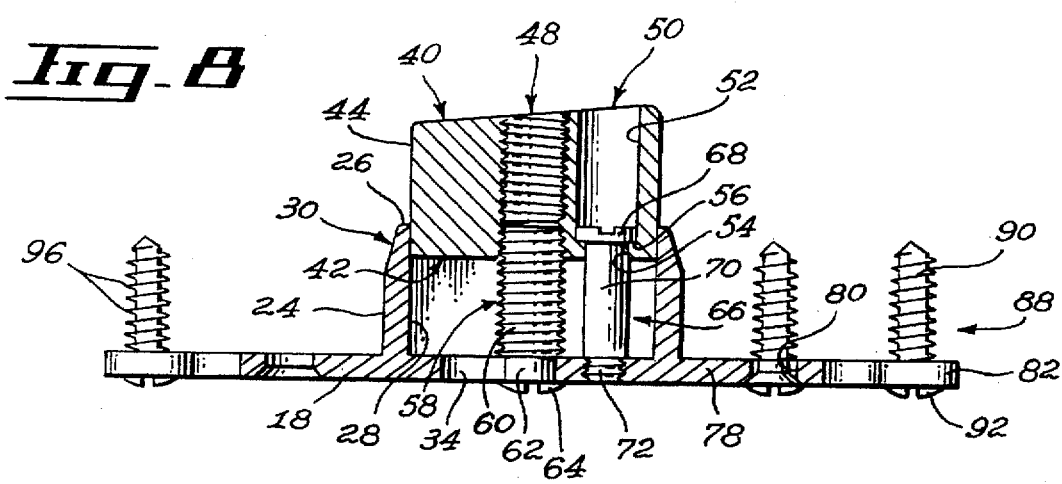
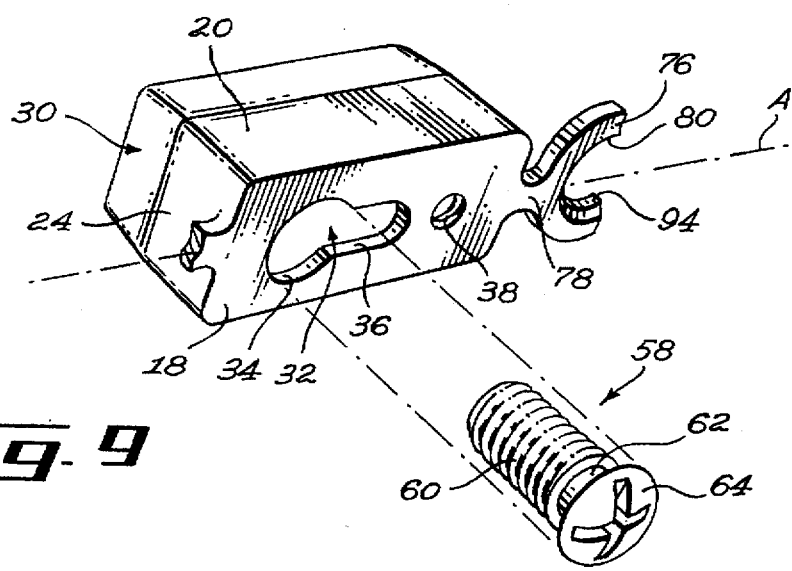

VOCAL CORD MEDIALIZING DEVICE

FIELD OF THE INVENTION

The present invention relates to the field of prosthesis devices and is particularly concerned with a device for medializing a paralyzed vocal cord.

BACKGROUND OF THE INVENTION

Vocal cords are formed by two folds of the lining membrane of the larynx positioned adjacent the opening of the glottis. Vocal cords are normally movable between a relatively closed convergent position located adjacent the middle of the larynx, and a relatively opened divergent position.

Phonation generally occurs when the vocal cords are in their convergent position, causing their respective edges to vibrate in the air stream. In their convergent position, the vocal cords at least partially obstruct the flow of air, thus detrimentally affecting the breathing efficiency. Breathing is facilitated when the phonation is interrupted to enable the vocal cords to move to their divergent position.

Consequently, during a normal vocal cord operation, the vocal cords undergo a dynamic movement between their convergent and divergent positions to respectively enable a person to phonate with good volume and breathe efficiently.

Movement of the vocal cords between their convergent and divergent positions is controlled, at least partially, by the laryngeal nerve that runs along the neck. Damage to the laryngeal nerve by trauma, surgery or a tumor can lead to a condition known as unilateral vocal cord paralysis wherein the associated vocal cord no longer functions properly and rests flacidly to the side of the larynx.

Although the remaining vocal cord is functional, it cannot crossover the midline of the larynx to press against the paralyzed vocal cord and form sound properly. The patients affected by unilateral vocal cord paralysis therefore suffer from disphonia. They have a horse breathy voice, they have difficulty raising their voices or coughing, and often aspirate fluids when swallowing.

In order to treat unilateral vocal cord paralysis, various methods and structures have been proposed to artificially move the paralyzed vocal cords towards the midline of the larynx, where the functional vocal cord can press against it. U.S. Pat. No. 3,818,894 issued in 1974 to Ceskoslovenska Akademie Zved discloses a water expandable reed-like structure that is adapted to be implanted in a dry state into the paralyzed vocal cord. After implantation, the reed-like structure undergoes a spunge-like expansion that increases the size of the paralyzed vocal cord and changes its position to a desired phonation position that also permits breathing.

Another known method of treatment for vocal cord paralysis includes the injection of a gel foam into the paralyzed vocal cord to increase its size and thus change the vocal cord position to one which permits stronger phonation without obstructing breathing. Both these methods suffer from at least two major drawbacks in that they do not allow for a precise positioning of the vocal cord and for a post-surgical adjustment of the position of the vocal cord.

U.S. Pat. No. 5,197,982 issued Mar. 30, 1993, to Goldsmith, III et al. teaches an adjustable prosthetic device including an actuator member for locating a paralyzed vocal cord in a predetermined phonation position. The device also includes a support member for supporting the actuator member in a predetermined position approximate the paralyzed vocal cord. A fluid input/withdrawal station for introducing or removing fluid from engagement with the actuator member enables the actuator member to change the location of the paralyzed vocal cord.

The support member that supports the actuator member can be hung to a thyroid cartilage or pass through the thyroid cartilage. Although efficient in providing a structure that can be adjusted postoperatively without need for further surgery, the device disclosed in U.S. Pat. No. 5,197,982 suffers from at least three drawbacks. First, its inherently complex structure generates a relatively high manufacturing cost. Second, the use of a fluid expandable shell does not allow for precise positioning of the vocal cord. Third, the use of a fluid expandable shell presents inherent leakage risks.

Another method of medializing a paralyzed vocal cord involves the injection of the paralyzed vocal cord with aliquots of TEFLON (registered trademark of Dupont) paste which expand the vocal cord towards the midline of the larynx. This method however suffers from the fact that the TEFLON injection does not provide for precise positioning of the vocal cord and also from the fact that it is difficult to estimate the exact amount and location of each required aliquot of paste. The method also suffers from the fact that there exists a potential risk of TEFLON paste migration and of a formation of granulation tissue.

In another known method of treatment of vocal cord dysfunction, a laryngoplasty is performed during which an implant such as a silicon block is installed between the thyroid cartilage and the paralyzed vocal cord to medialize the vocal cord. The shaping and sizing of the implant are usually manual procedures performed by the surgeon on an empirical basis. The prosthesis is formed based on an estimate of the amount of medialization needed by the patient.

A preliminary version of the implant is inserted between the vocal cord and the thyroid cartilage and the patient's phonation ability is evaluated. If needed, the prosthesis is removed and resized before being inserted again between the vocal cord and the thyroid cartilage for further evaluation of the patient's phonation ability. This method suffers from the fact that each insertion and subsequent removal of an implant can cause trauma and tissue edema. Swelling of the tissue often leads to a false determination of optimum size for an implant.

U.S. Pat. No. 5,201,765 discloses a preformed and pre-sized prosthesis member along with a tool for displacing a vocal cord to an optimal phonation position and measuring the amount of displacement to permit use of the presized prosthesis. It is however difficult to fine tune the patient's optimal voice with the technique. It is indeed difficult to customize the shape of the silastic block during the surgical procedure. Furthermore, postoperative adjustment of the device requires further surgery.

U.S. Pat. No. 5,306,298 naming Frederic A. Godley III et al. as inventors discloses a medializing device comprising a rectangular anchoring plate, a prosthesis member, and a pair of adjustment screws which threadaly engage a pair of threaded apertures in the anchoring plate. The adjustment screws are rotatably connected to the prosthesis member. The device suffers from a set of drawbacks. First, the adjustment screws being threadaly engaged in corresponding apertures provided in the anchoring plate must be moved along their longitudinal axis relatively to the plate during adjustment.

When the prosthesis member is adjusted in a position other than its fully protracted position, a segment of the adjustment screws protrudes outwardly from the anchoring plate, thus coming into contact with surrounding body tissues. The segment of the adjustment screws protruding from the anchoring plate thus forms an unesthetical and unpleasant bulge and can lead to irritation of the surrounding body tissues including the adjacent strap muscles.

Second, after the device is initially installed, surrounding soft tissues will have a tendency to fill the gaps created respectively between the adjustment screw heads and the anchoring plate, as well as between the anchoring plate and the prosthesis member. Once these gaps have been filled, any movement of the adjustment screws and of the prosthesis members to which they are rotatably connected will cause some of the soft tissues having filled the gaps to be squeezed.

Indeed, retraction of the prosthesis member causes the tissue between the prosthesis member and the anchoring plate to be squeezed, while retraction of the prosthesis member causes the tissues between the adjustment screw heads and the anchoring plate to be squeezed. Squeezing of the tissues in turn causes trauma to the latter.

Third, the use of an anchoring plate is also not particularly well suited to the relatively rugged outer surface of the thyroid cartilage. Furthermore, the plate and the anchoring screws used to attach the plate to the cartilage create a structural stress in the cartilage.

Accordingly, there is a need for an improved vocal cord medializing device that could allow for a simple yet efficient adjustment of the position of the paralyzed vocal cord, while also allowing for postoperative adjustments without trauma to the surrounding body tissues and with minimum discomfort to the patient.

SUMMARY OF THE INVENTION

It is an object of the present invention to provide an improved vocal cord medializing device.

In accordance with one aspect of the present invention, there is provided a vocal cord medializing device for medializing a vocal cord, the vocal cord being located inside a larynx, the larynx including a thyroid cartilage and a window formed in the thyroid cartilage adjacent the vocal cord, the device comprising: a hollow guiding sleeve defining a sleeve channel, the sleeve channel extending between a sleeve proximal end and a sleeve distal end, the guiding sleeve being configured and sized so as to be insertable inside the window; a sleeve base wall extending across the sleeve proximal end for closing the latter; a biasing block slidably inserted in the sleeve channel, the biasing block being movable between a retracted position wherein the biasing block is in a substantially proximal relationship relatively to the sleeve base wall and a protracted position wherein the biasing block is in a substantially spaced relationship relatively to the sleeve base wall; an adjustment screw for moving the biasing block between the protracted and retracted positions, the adjustment screw being rotatably attached to the sleeve base wall and threadaly attached to the biasing block, the adjustment screw having a screw longitudinal axis; a fixing means for fixing the device to the thyroid cartilage with the guiding sleeve inserted in the window, the fixing means extending laterally from the sleeve base wall; whereby a rotation of the adjustment screw causes the biasing block to slide inside the sleeve channel without causing the adjustment screw to move along the screw longitudinal axis relatively to the sleeve base wall.

Conveniently, the sleeve base wall has a substantially rectangular and flat configuration defining a pair of transversally opposed base wall side peripheral edges and a pair of longitudinally opposed base wall end peripheral edges, the guiding sleeve including a pair of opposed sleeve side walls extending integrally and substantially perpendicularly from the base wall side peripheral edges and a pair of opposed sleeve end walls extending integrally and substantially perpendicularly from the base wall end peripheral edges, the sleeve side walls and the sleeve end walls merging integrally to form the sleeve channel.

Preferably, the guiding sleeve has a sleeve outer surface, the sleeve outer surface having an inwardly tapering section in a direction leading away from the sleeve base wall, the inwardly tapering section being positioned adjacent the sleeve distal end.

Typically, the adjustment screw has an adjustment screw longitudinal axis, an adjustment screw head, an adjustment screw threaded segment and a non-threaded adjustment screw spacing segment extending integrally between the adjustment screw head and the adjustment screw threaded segment; the sleeve having a sleeve first aperture extending therethrough, the biasing block having a threaded block first aperture extending therethrough, the adjustment screw being mounted to both the sleeve base wall and the biasing block with the adjustment screw threaded segment threadaly engaging the block first aperture, the adjustment screw spacing segment rotatably extending through the sleeve first aperture and the adjustment screw head abuttingly contacting the sleeve base wall, whereby a rotation of the adjustment screw causes a relative displacement between the guiding sleeve and the biasing block without causing a relative displacement between the adjustment screw and the guiding sleeve about the adjustment screw longitudinal axis.

Conveniently, the sleeve first aperture has a larger aperture segment that extends integrally into a radially contiguous smaller aperture segment, the larger aperture segment being configured and sized so as to allow through passage of the adjustment screw head, the smaller aperture segment being configured and sized so as to prevent the through passage of the adjustment screw head, whereby the adjustment screw spacing segment is adapted to extend through the smaller aperture segment of the sleeve first aperture with the adjustment screw head abuttingly contacting the sleeve base wall adjacent the smaller aperture segment so as to prevent a longitudinal axial displacement of the adjustment screw.

Preferably, the device further comprises a sleeve second aperture, the sleeve second aperture being provided with a sleeve second aperture internal thread, the sleeve second aperture extending through the sleeve base wall; a block second aperture extending through the biasing block, the block second aperture being positioned so as to be in a substantially coaxial relationship with the sleeve second aperture; the block second aperture being configured so as to define an inwardly projecting second aperture abutment shoulder; a stopper screw, the stopper screw having a stopper screw head, a stopper screw threaded segment and a non-threaded stopper screw spacing segment extending integrally between the stopper screw head and the stopper screw threaded segment, the stopper screw head being configured and sized so as to be slidably insertable into the block second aperture and so as to abut against the second aperture abutment shoulder, the stopper screw threaded segment being configured and sized so as to threadaly engage the sleeve second aperture internal thread, whereby the stopper screw head is adapted to slide inside the second block aperture when the biasing block is moved between the retracted position and the protracted position, the stopper screw head being adapted to abut against the second aperture abutment shoulder when the biasing block is in a fully protracted position so as to prevent further protraction of the biasing block.

Conveniently, the block second aperture has a second aperture larger segment and an integrally extending second aperture smaller segment. The second aperture abutment shoulder is defined by the junction between the second aperture larger segment and the second aperture smaller segment.

Typically, the biasing block has a substantially parallelepiped-shaped configuration defining a biasing block abutting surface and an opposed biasing block base surface, the biasing block abutting surface being provided with an anti-skid texture formed thereon.

Preferably, the anti-skid texture is formed by a set of relatively small protuberances.

Preferably, the abutting surface is angled relatively to the base surface.

Typically, the fixing means includes a pair of substantially "Y"-shaped anchoring structures, the anchoring structures extending integrally and substantially outwardly from the opposed end peripheral edges of the sleeve base wall.

Typically, each of the anchoring structures includes a substantially annular-shaped main fixing ring and a pair of substantially annular-shaped auxiliary fixing rings, the auxiliary fixing rings being substantially symmetrically disposed relatively to the main fixing ring, the main fixing rings and the auxiliary fixing rings being adapted to receive a corresponding set of anchoring screws.

Conveniently, the main fixing ring is connected to an adjacent end peripheral edge by a main connecting member. The auxiliary fixing rings are connected to an adjacent main fixing ring by corresponding auxiliary connecting members.

Preferably, the main connecting members and the auxiliary connecting members are made of a substantially flat and thin bendable strip of material so as to allow the main fixing rings and the auxiliary fixing rings to be moved relatively to each other in various geometrical planes.

Preferably, the main connecting members are positioned substantially aligned with the base wall longitudinal axis. The auxiliary connecting members are positioned so as to form an angle having a value substantially in the range of forty degrees relatively to the base wall longitudinal axis.

Conveniently, the main fixing rings and the auxiliary fixing rings are each provided with an annular recess formed therein.

Typically, the anchoring structures have a thickness substantially in the range of 1,5 millimeters.

Advantages of the present invention include the fact that the medializing device allows for a precise adjustment of the position of the paralyzed vocal cord.

Another advantage is that the device allows for postoperative adjustment of the position of the paralyzed vocal cord through a simple procedure.

A further advantage relates to the fact that postoperative adjustment can be effected without damaging surrounding tissues.

A still further advantage of the present invention relates to the fact that the device does not create an unesthetical, unpleasant and potentially irritating bulge once installed.

BRIEF DESCRIPTION OF THE DRAWINGS

An embodiment of the present invention will now be described, by way of example, in reference to the following drawings in which:

FIG. 7: in a longitudinal cross-sectional view taken along arrows 7—7 of FIG. 3, illustrates a medializing device in accordance with an embodiment of the present invention with its biasing block in a retracted position;

FIG. 8: in a longitudinal cross-sectional view, illustrates the medializing device of FIG. 7 with its biasing block in a protracted position;

FIG. 9: in a bottom perspective view with sections taken out, illustrates a guiding sleeve, an adjustment screw and a portion of the fixing components part of a medializing device in accordance with an embodiment of the present invention.

Similar references are used in different views to denote similar components.

DETAILED DESCRIPTION

Figure 1:
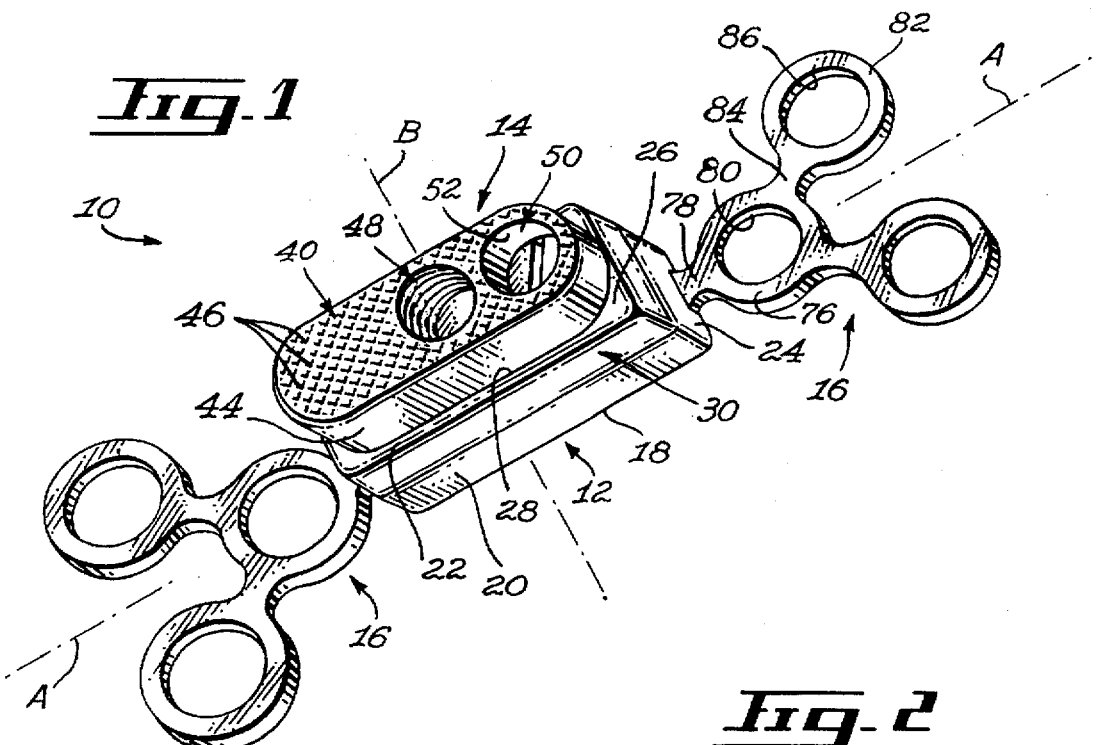
FIG. 1: in a front perspective view, illustrates a medializing device in accordance with an embodiment of the present invention.

Referring to FIG. 1, there is shown a vocal cord medializing device 10 in accordance with an embodiment of the present invention. The medializing device 10 has a guiding sleeve 12, a biasing block 14 slidably inserted in the guiding sleeve 12 and a fixing means 16 for fixing the guiding sleeve 12 to an intended patient, as will be hereinafter described.

The guiding sleeve 12 typically has a substantially parallelepiped-shaped general configuration. The guiding sleeve 12 has a substantially rectangular and flat sleeve base wall 18 defining a base wall longitudinal axis A and a perpendicularly disposed base wall transversal axis B.

A pair of opposed sleeve side walls 20 (only one of which is shown in FIG. 1) extends integrally and substantially perpendicularly from the transversely opposed side peripheral edges of the sleeve base wall 18 to a corresponding pair of side wall distal peripheral edges 22.

A pair of opposed sleeve end walls 24 (only one of which is shown in FIG. 1) extends integrally and substantially perpendicularly from the longitudinally opposed longitudinal peripheral edges of the sleeve base wall 18 to a corresponding pair of end wall distal peripheral edges 26.

The sleeve side walls 20 and the sleeve end walls 24 merge integrally to form a sleeve channel 28 that extends from the sleeve base wall 18 to the side wall distal peripheral edges 22 and the end wall distal peripheral edges 26, in a substantially perpendicular orientation relatively to the base wall longitudinal axis A and the base wall transversal axis B. The sleeve channel 28 is closed at one end thereof by the sleeve base wall 18.

The inner surfaces of the sleeve side walls 20 and the sleeve end walls 24 are typically configured so that the sleeve channel 28 has a generally rectangular configuration with substantially rounded corner edges. The corner edges have relatively large curvature radiuses so as to form smooth edges.

It should be understood that although the guiding sleeve 12 is shown as having a substantially parallelepiped-shaped configuration, it could also have a cylindrical or any suitable configuration defining a sleeve channel closed at one end thereof without departing from the scope of the present invention.

The outer surfaces of the sleeve side walls 20 and the sleeve end walls 24 are bevelled inwardly adjacent their respective side wall distal peripheral edges 22 and end wall distal peripheral edges 26 so as to define a sleeve bevelled section 30.

Figure 3:
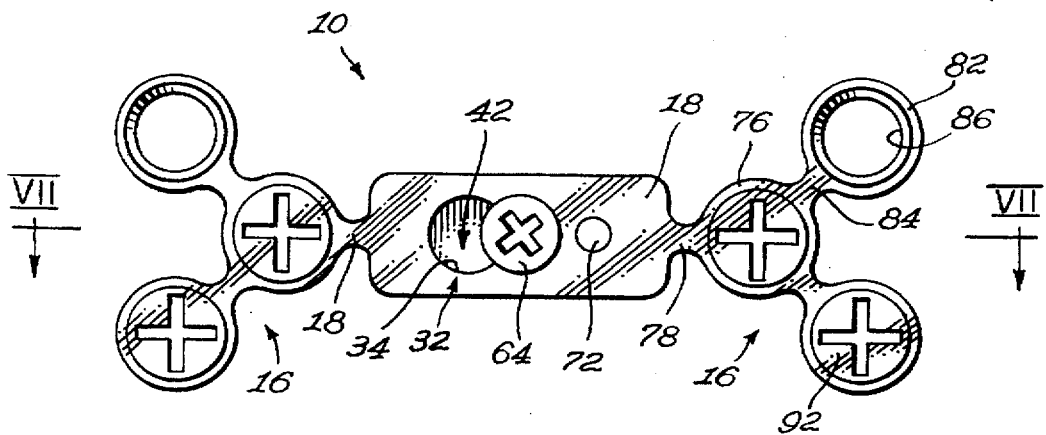
FIG. 3: in a bottom view, illustrates the medializing device of FIG. 1.

As illustrated more specifically in FIG. 3 and in FIGS. 7 through 9, the sleeve base wall 18 has a sleeve first aperture 32 extending therethrough. The sleeve first aperture 32 has a larger aperture segment 34 that extends integrally into a radially contiguous smaller aperture segment 36. The size of the larger aperture segment 34 is relatively larger than the size of the smaller aperture segment 36 for reasons which will be hereinafter disclosed.

The sleeve base wall 18 also has a sleeve second aperture 38 extending therethrough. The peripheral edge of the sleeve second aperture 38 is provided with a thread. The larger aperture segment 34, the smaller aperture segment 36 and the sleeve second aperture 38 are typically aligned along the base wall longitudinal axis A.

The biasing block 14 is configured and sized so as to be slidably and fittingly insertable into the sleeve channel 28. The biasing block 14 thus has a substantially parallelepiped-shaped general configuration with relatively smooth rounded edges. Optionally, the biasing block 14 may have a relatively wedge-shaped general configuration. The biasing block 14 has a block biasing surface 40 and an opposed block base surface 42.

A biasing block peripheral surface 44 extends between the block biasing surface 40 and the block base surface 42. The biasing block peripheral surface 44 is configured and sized so as to fit into the interior surface defined by the sleeve side walls 20 and the sleeve end walls 24.

The block biasing surface 40 is provided with an anti-skid texture formed thereon. Typically, the anti-skid texture consists in an array of relatively small protuberances 46 that extend integrally and substantially outwardly from the block biasing surface 40.

The block biasing surface 40 may either be substantially parallel to the block base surface 42 or angled relatively to the latter, as illustrated more specifically in FIGS. 7 and 8. The phantom lines indicated by the reference character C in FIG. 7 are used to indicate, by way of example, various possible orientations of the block biasing surface 40.

A block first aperture 48 extends through the biasing block 14 from the block biasing surface 40 to the block base surface 42. The block first aperture 48 is positioned so as to be substantially in register with the smaller aperture segment 36 when the biasing block 14 is inserted in the sleeve channel 28. The inner surface of the block first aperture 48 is provided with a thread.

A block second aperture 50 extends through the biasing block 14 from the block biasing surface 40 to the block base surface 42. The block second aperture 50 is positioned so as to be in a coaxial relationship with the sleeve second aperture 38 when the biasing block 14 is inserted in the sleeve channel 28.

The block second aperture 50 has a second aperture larger segment 52 extending through the block biasing surface 40. The second aperture larger segment 52 extends integrally into a longitudinally contiguous second aperture smaller segment 54 that extends through the block base surface 42. The second aperture larger segment 52 is relatively wider and longer than the second aperture smaller segment 54.

The second aperture larger segment 52 being larger than the second aperture smaller segment 54, the junction between the second aperture larger segment 52 and the second aperture smaller segment 54 defines a second aperture abutment shoulder 56. Both the block first aperture 48 and the block second aperture 50 typically have a substantially circular cross-sectional configuration.

An adjustment screw 58 threadaly connects the biasing block 14 to the sleeve base wall 18. The adjustment screw 58 has an adjustment screw threaded segment 60 that extends integrally into a non-threaded adjustment screw spacing segment 62. The adjustment screw spacing segment 62 in turn extends integrally into a substantially thin adjustment screw head 64.

As illustrated more specifically in FIGS. 7 and 8, the length of the adjustment screw threaded segment 60 corresponds substantially to the length of the block first aperture 48, while the length of the adjustment screw spacing segment 62 corresponds substantially to the thickness of the sleeve base wall 18.

The adjustment screw 58 is adapted to be mounted to the guiding sleeve 12 and to the biasing block 14 with the adjustment screw threaded segment 60 threadaly engaging the threads of the inner surface of the block first aperture 48, the adjustment screw spacing segment 62 rotatably extending through the sleeve first aperture 32 and the adjustment screw head 64 abuttingly contacting the exterior surface of the sleeve base wall 18.

A stopper screw 66 slidably connects the biasing block 14 to the sleeve base wall 18. The stopper screw 66 has a stopper screw head 68 that is configured and sized so as to be slidably insertable into the second aperture larger segment 52. The stopper screw head 68 extends integrally into a non-threaded stopper screw spacing segment 70. The stopper screw spacing segment 70 is sized so as to be slidably insertable in the second aperture smaller segment 54.

The stopper screw spacing segment 70 extends integrally into a smaller stopper screw threaded segment 72. The junction between the stopper screw spacing segment 70 and the stopper screw threaded segment 72 defines a stopper screw abutment shoulder 74.

The length of the stopper screw spacing segment 70 is sized so that the stopper screw abutment shoulder 74 abuts against the inner surface of the sleeve base wall 18 when the stopper screw head 78 abuts against the second aperture abutment shoulder 56. The stopper screw threaded segment 72 is sized so as to threadaly engage the threads of the sleeve second aperture 38.

The stopper screw 66 is adapted to be mounted to the biasing block 14 and to the guiding sleeve 12 with the stopper screw head 68 slidably inserted in the second aperture larger segment 52, the stopper screw spacing segment 70 slidable engaged in the second aperture smaller segment 54 and the stopper screw threaded segment 72 threadaly anchored to the threads of the sleeve second aperture 38.

The fixing means 16 typically includes a pair of substantially "Y"-shaped anchoring structures extending integrally and outwardly from the longitudinal end peripheral edges of the sleeve base wall 18.

Each anchoring structure includes a substantially annular-shaped main fixing ting 76 that is connected to the end peripheral edges of the sleeve base wall 18 by a main connecting member 78. Each main fixing ting 76 defines a main ting inner aperture 80 typically having a substantially disk-shaped general configuration. The main connecting members 78 and the main fixing rings 76 are positioned so that the main connecting members 78 extend substantially aligned with the base wall longitudinal axis A and so that the center of the main ting inner aperture 80 is substantially in register with the base wall longitudinal axis A.

A pair of substantially annular-shaped auxiliary fixing rings 82 is connected to each main fixing ting 76 by a corresponding pair of integrally extending auxiliary connecting members 84. The auxiliary fixing tings 82 each define a corresponding substantially disk-shaped auxiliary ring inner aperture 86.

Figure 2:
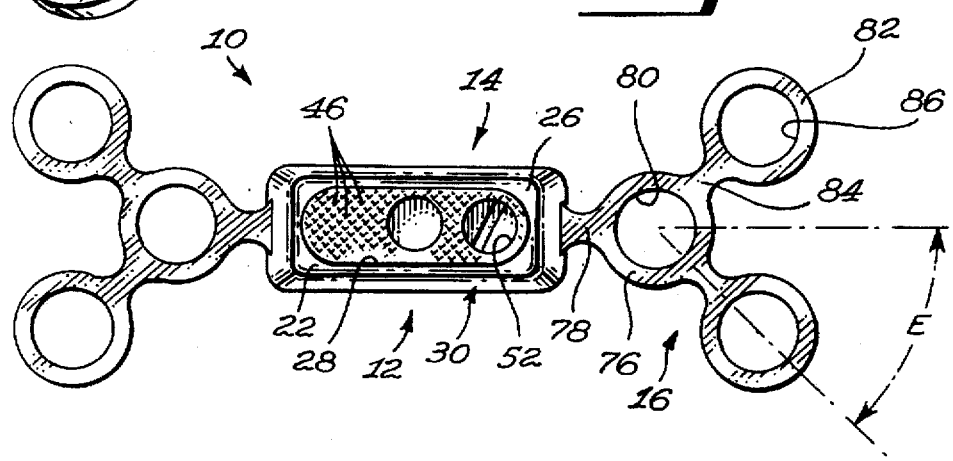
FIG. 2: in a top view, illustrates the medializing device of FIG. 1.

As illustrated more specifically in FIG. 2, the auxiliary connecting members 84 and the auxiliary fixing rings 82 are positioned so that an axis intercepting the center of the main ring inner aperture 80 and an adjacent auxiliary ring inner aperture 86 defines an angle E with the base wall longitudinal axis A. The angle E typically has a value substantially in the range of forty degrees.

As illustrated in FIG. 3, the main fixing rings 76 and the auxiliary fixing rings 82 are each provided with an annular recess 94 adjacent the corresponding main ring inner aperture 80 and the auxiliary ring inner aperture 86.

A set of anchoring screws 88 is adapted to be inserted in the main fixing rings 76 and the auxiliary fixing rings 82. Each anchoring screw 88 has an anchoring screw threaded stem 90 and an integrally extending substantially thin anchoring screw head 92. The anchoring screw threaded stem 90 is characterized by the spacing between the threads.

Figure 4:
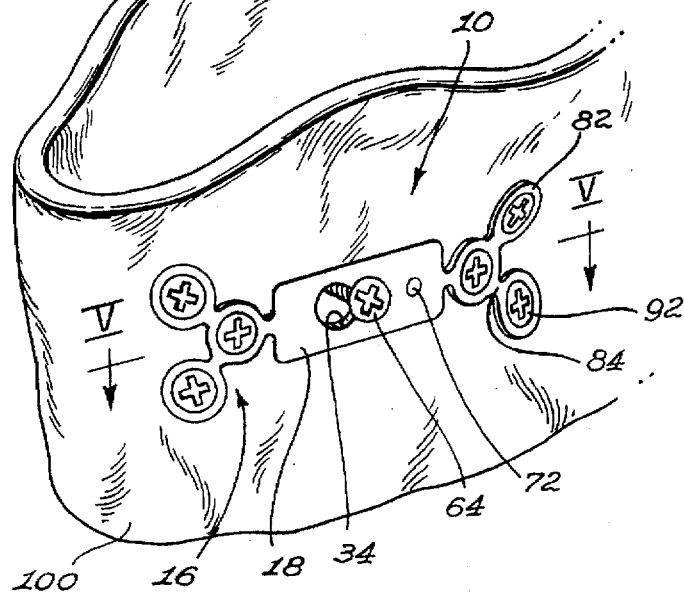
FIG. 4: in a perspective schematic view, illustrates a medializing device in accordance with an embodiment of the present invention implanted on a thyroid cartilage.
Figure 5:
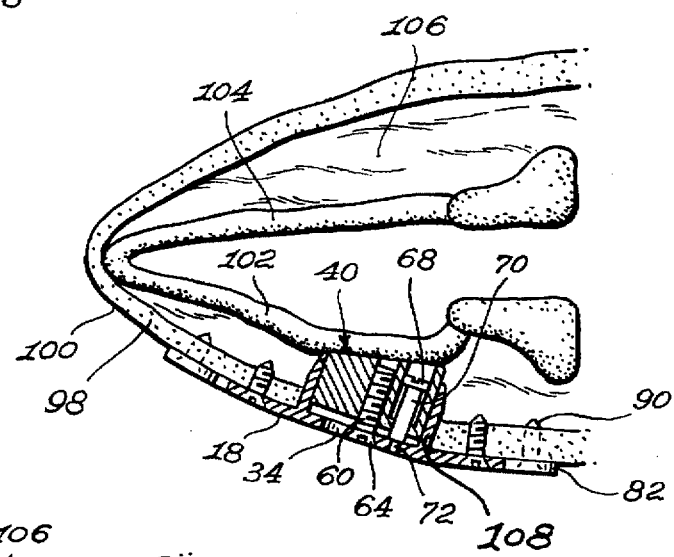
FIG. 5: in a cross-sectional view taken along arrows 5—5 of FIG. 4, illustrates a medializing device in accordance with an embodiment of the present invention mounted on a thyroid cartilage with its biasing block in a retracted position.
Figure 6:
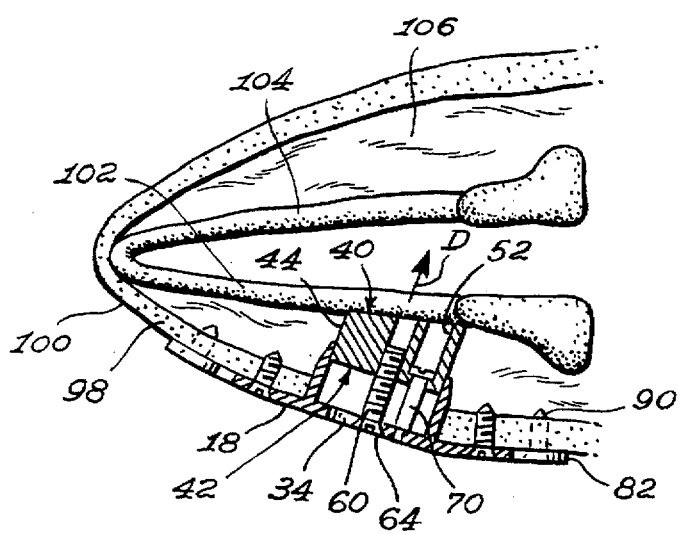
FIG. 6: in a cross-sectional view, illustrates the medializing device of FIG. 5 with its biasing block in a protracted position.

Referring now more specifically to FIGS. 4 through 6, the reference numeral 98 is used to designate the schematical representation of a section of the thyroid cartilage which surrounds the larynx of an intended patient.

The section of the thyroid cartilage 98 that surrounds the larynx has a substantially broad "V"-shaped cross-sectional configuration when looked at in a horizontal plane. The outer surface 100 of the thyroid cartilage 98 defines a substantially accidented relief.

The reference numeral 102 is used in FIGS. 5 and 6 to designate a paralyzed vocal cord having a relatively flacid consistency and a relatively irregular configuration. The reference numeral 104 is used to designate an opposed healthy vocal cord.

When both vocal cords are healthy, they form a substantially "V"-shaped configuration when looked at in cross-section from a horizontal plane. The "V"-shaped configuration of the healty vocal cords is relatively more acute than the "V"-shaped configuration formed by the thyroid cartilage 98.

A volume of soft tissues 106 fills the area defined between the vocal cords 102 and 104 and the thyroid cartilage 98.

To implant the medializing device 10 on a patient, an incision is made in the neck of the patient on the side of the paralyzed vocal cord 102. The strap muscles (not shown) are then separated to reveal the thyroid cartilage 98.

The thyroid cartilage 98 is cut so as to form a substantially rectangular window 108 adjacent the paralyzed vocal cord 102. The window 108 is configured and sized so as to fittingly receive the guiding sleeve 12, as will be hereinafter disclosed.

The cutting of the window 108 in the thyroid cartilage 98 forms a corresponding panel of cartilage (not shown) that can either be removed, as illustrated in FIGS. 5 and 6, or alternatively remain attached to the underlying soft tissues 106.

The guiding sleeve 12 is then slidably inserted into the window 108. The guiding sleeve 12 is adapted to facilitate the manipulation of the medializing device 10 and its implantation in the window 108. The sleeve bevelled section 30 and the relatively smooth corner edges of the guiding sleeve 12 are adapted to further facilitate the insertion of the guiding sleeve 12 into the window 108.

The guiding sleeve 12 is inserted into the window 108 until the fixing means 16 abuttingly contacts the outer surface 100 of the thyroid cartilage 98. As mentioned previously, the outer surface 100 of the thyroid cartilage 98 forms a substantially accidented relief. One of the main characteristics of the present invention resides in that the fixing means 16 is specifically configured so as to fittingly conform to such a relief.

Indeed, the main connecting members 78 and the auxiliary connecting members 84 are both made of substantially flat and thin segments of bendable material so as to allow the main fixing tings 76 and the auxiliary fixing rings 82 to be moved relatively to each other in various geometrical planes.

The bendable nature of the main connecting members 78 and the auxiliary connecting members 84, combined with the substantially "Y"-shaped configuration of the fixing means 16, allows the fixing means 16 to be customized to the specific relief of the outer surface 100 of each patient. In order to adapt the fixing means 16 to the various reliefs, the main connecting members 78 and the auxiliary connecting members 84 are bent and twisted so that the corresponding main fixing rings 76 and auxiliary fixing tings 82 lie in a substantially flush abutting contact with the outer surface 100.

Once the main fixing rings 76 and the auxiliary fixing rings 82 are properly positioned, guide holes (not shown) are drilled into the thyroid cartilage, in register with the center of the main ring inner apertures 80 and the auxiliary ring inner apertures 86.

The anchoring screw threaded stems 90 are then threadaly inserted into the guide holes to secure the fixing means 16 to the thyroid cartilage 98. The use of six anchoring screws 88 that are spaced from one another and form a pair of substantially "Y"-shaped patterns improves the retention properties of the fixing means 16 and minimizes the structural stress imposed to the thyroid cartilage 98 by the anchoring screws 88. The substantially "Y"-shaped pattern also minimizes the rotation of the sleeve base wall 18 about the base wall longitudinal axis A which, in turn, improves the stability of the medializing device 10.

The anchoring screws 88 are threaded in the thyroid cartilage 98 until the anchoring screw heads 92 abut against the annular recesses 94. The anchoring screw heads 92 are configured so as to form a substantially continuous surface with the outer surfaces of the main fixing rings 76 and the auxiliary fixing rings 82, thus preventing the formation of protuberances. Typically, the fixing means 16 is configured so as to present a thickness substantially in the range of 1,5 millimeters, thus minimizing overall discomfort to the patient and preventing irritation of the adjacent strap muscles.

As mentioned previously, the threads of the anchoring screw threaded stems 90 are specifically configured and spaced so as to firmly grip into the thyroid cartilage 98. Typically, the threads formed on the anchoring screw threaded stems are spaced by a greater distance than the threads found on conventional surgical screws. The increased spacing between the threads facilitates installation, minimizes stripping and provides for an improved grip.

Once the medializing device 10 is firmly secured to the outer surface 100 of the thyroid cartilage 98, the adjustment screw 58 is used to adjust the position of the biasing block 14 relatively to the guiding sleeve 12 and to the paralyzed vocal cord 102.

Since the adjustment screw threaded segment 60 threadaly engages the threads present on the inner surface of the block first aperture 48, a rotation of the adjustment screw head 64 in one of two directions will cause a corresponding protraction or retraction of the biasing block 14 in the sleeve channel 28.

Furthermore, since the adjustment screw spacing segment 62 is non-threadaly engaged in the sleeve base wall 18, the rotation of the adjustment screw head 64 will not cause any longitudinal movement of the adjustment screw 58 relatively to the guiding sleeve 12 that would, in turn, cause a protuberance.

As mentioned previously, another main advantage of the present invention relates to the fact that since the adjustment screw 58 does not move longitudinally relatively to the guiding sleeve 12, the adjustment screw head 64 remains in contact with the sleeve base wall 18, thus preventing the squeezing of surrounding body tissues between the adjustment screw head 64 and the sleeve base wall 18.

A still further advantage of the present invention relates to the fact that the sleeve side walls 20 and the sleeve end walls 24 prevent the soft tissues 106 from penetrating in the volume created between the block base surface 42 and the sleeve base wall 18 when the biasing block 14 is not in its fully retracted position. Since the soft tissues 106 cannot penetrate in the spacing between the block base surface 42 and the sleeve base wall 18, the soft tissues cannot be squeezed by the biasing block 14 when the latter is retracted during adjustment of the device 10.

As illustrated in FIG. 5, the adjustment screw 58 is thus adapted to effectively position the block biasing surface 40 in an abutting relationship with the paralyzed vocal cord 102. Once the block biasing surface 40 abuttingly contacts the paralyzed vocal cord 102, the adjustment screw 58 is again rotated so as to displace the paralyzed vocal cord 102 away from the thyroid cartilage 98 to an optimum phonation position determined by the physician.

Rotation of the adjustment screw 58 thus enables the biasing block 14 to move the paralyzed vocal cord 102 from its receeded and relatively divergent paralyzed position to a desired convergent phonation position, as illustrated by the arrow D in FIG. 6. The adjustment screw 58 is configured with threads allowing for a precise adjustment of the position of the biasing block The anti-skid texture formed on the block biasing surface 40 prevents the paralyzed vocal cord 102 from slipping out of position relatively to the block biasing surface 40. The anti-skid texture being preferably formed by relatively small protuberances 46, it also increases the contact area between the block biasing surface 40 and the paralyzed vocal cord 102 and thus enhances the healing process.

The guiding sleeve 12 is adapted to guide the biasing block 14 in its protracting and retracting movement, as well as to ensure that the latter remains properly aligned once optimally located. The guiding sleeve 12 prevents the biasing block 14 from being rotated, twisted or otherwise displaced from its proper alignment relatively to the sleeve base wall 18.

The stopper screw head 68 is adapted to slide in the second aperture larger segment 52 during the retraction and protraction of the biasing block 14. When the biasing block 14 is in its fully protracted position illustrated in FIG. 6, the stopper screw head 68 abuttingly contacts the stopper screw abutment shoulder 74, thus preventing further protraction of the biasing block 14.

The larger aperture segment 34 provided in the sleeve base wall 18 is adapted to allow through passage of the adjustment screw 58 so as to facilitate the installation of the biasing block 14 into the sleeve channel 28 during assembly of the medializing device 10.

As mentioned previously, a pair of healthy vocal cords in their substantially convergent position typically form a more acute "V"-shaped configuration than the "V"-shaped cross-sectional configuration of the corresponding thyroid cartilage. Accordingly, to medially displace a paralyzed vocal cord so that it rests evenly in the midline, the posterior section of the vocal cord must be displaced more than the anterior section. The block biasing surface 40 is thus typically angled relatively to the block base surface 42. The orientation of the block biasing surface 40, indicated by the reference character C in FIG. 7, is typically chosen so as to conform to the specific morphological characteristics of each patient.

The medializing device is typically manufactured out of a bio-compatible and bio-integrable material such as a titanium alloy.

Numerous modifications, variations and adaptations may be made to the particular embodiment of the invention hereinabove described without departing from the scope of the invention as defined in the claims.

The embodiments of the invention in which an exclusive privilege or property is claimed are defined as follows:

1. A vocal cord medializing device for medializing a vocal cord, said vocal cord being located inside a larynx, said larynx including a thyroid cartilage and a window formed in said thyroid cartilage adjacent said vocal cord, said device comprising:

a hollow guiding sleeve defining a sleeve channel, said sleeve channel extending between a sleeve proximal end and a sleeve distal end, said guiding sleeve being configured and sized so as to be insertable inside said window;

a sleeve base wall extending across said sleeve proximal end for closing the latter;

a biasing block slidably inserted in said sleeve channel, said biasing block being movable between a retracted position wherein said biasing block is in a substantially proximal relationship relatively to said sleeve base wall and a protracted position wherein said biasing block is in a substantially spaced relationship relatively to said sleeve base wall;

an adjustment screw for moving said biasing block between said protracted and retracted positions, said adjustment screw being rotatably attached to said sleeve base wall and threadaly attached to said biasing block, said adjustment screw having a screw longitudinal axis;

a fixing means for fixing said device to said thyroid cartilage with said guiding sleeve inserted in said window, said fixing means extending laterally from said sleeve base wall;

whereby a rotation of said adjustment screw causes said biasing block to slide inside said sleeve channel without causing said adjustment screw to move along said screw longitudinal axis relatively to said sleeve base wall.

2. A device as recited in claim 1 wherein said sleeve base wall has a substantially rectangular and flat configuration defining a pair of transversely opposed base wall side peripheral edges and a pair of longitudinally opposed base wall end peripheral edges, said guiding sleeve including a pair of opposed sleeve side walls extending integrally and substantially perpendicularly from said base wall side peripheral edges and a pair of opposed sleeve end walls extending integrally and substantially perpendicularly from said base wall end peripheral edges, said sleeve side walls and said sleeve end walls merging integrally to form said sleeve channel.

3. A device as recited in claim 2 wherein said guiding sleeve has a sleeve outer surface, said sleeve outer surface having an inwardly tapering section in a direction leading away from said sleeve base wall, said inwardly tapering section being positioned adjacent said sleeve distal end.

4. A device as recited in claim 1 wherein said biasing block has a substantially parallelepiped-shaped configuration defining a biasing block abutting surface and an opposed biasing block base surface, said biasing block abutting surface being provided with an anti-skid texture formed thereon.

5. A device as recited in claim 4 wherein said anti-skid texture is formed by a set of relatively small protuberances.

6. A device as recited in claim 4 wherein said abutting surface is angled relatively to said biasing block base surface.

7. A vocal cord medializing device for medializing a vocal cord, said vocal cord being located inside a larynx, said larynx including a thyroid cartilage and a window formed in said thyroid cartilage adjacent said vocal cord, said device comprising:

a hollow guiding sleeve defining a sleeve channel, said sleeve channel being closed at one end thereof by a sleeve base wall, said guiding sleeve being configured and sized so as to be insertable inside said window;

a biasing block slidably inserted in said sleeve channel, said biasing block being movable between a retracted position wherein said biasing block is in a substantially proximal relationship relatively to said sleeve base wall and a protracted position wherein said biasing block is in a substantially spaced relationship relatively to said sleeve base wall;

an adjustment screw for moving said biasing block between said protracted and retracted positions, said adjustment screw being rotatably attached to said sleeve base wall and threadably attached to said biasing block, said adjustment screw having a screw longitudinal axis;

a fixing means for fixing said device to said thyroid cartilage with said guiding sleeve inserted in said window, said fixing means extending laterally from said sleeve base wall;

whereby a rotation of said ajustment screw causes said biases block to slide inside said sleeve channel without causing said screw to move along said screw longitudinal axis relatively to said sleeve base wall.

8. A vocal cord medializing device for medializing a vocal cord, said vocal cord being located inside a larynx, said larynx including a thyroid cartilage and a window formed in said thyroid cartilage adjacent said vocal cord, said device comprising:

a hollow guiding sleeve defining a sleeve channel, said sleeve channel extending between a sleeve proximal end and a sleeve distal end, said guiding sleeve being configured and sized so as to be insertable inside said window;

a sleeve base wall extending across said sleeve proximal end for closing the latter, a biasing block slidably inserted in said sleeve channel said biasing block being movable between a retracted position wherein said biasing block is in a substantially proximal relationship relative to said sleeve base wall and a protracted position wherein said biasing block is in a substantially spaced relationship relative to said sleeve basewall;

an adjustment screw for moving said biasing block between said protracted and retracted positions, said adjustment screw being rotatably attached to said sleeve base wall and threadedly attached to said biasing block, said adjustment screw having a screw longitudinal axis;

an adjustment screw head, an adjustment screw threaded segment and a non-threaded adjustment screw spacing segment extending integrally between said adjustment screw head and said adjustment screw threaded segment; said sleeve having a sleeve first aperture extending therethrough, said biasing block having a threaded block first aperture extending therethrough, said adjustment screw being mounted to both said sleeve base wall and said biasing block with said adjustment screw threaded segment threadedly engaging said block first aperture, said adjustment screw spacing segment rotatably extending through said sleeve first aperture and said adjustment screw head abuttingly contacting said sleeve base wall, whereby a rotation of said adjustment screw causes a relative displacement between said guiding sleeve and said biasing block without causing a relative displacement between said adjustment screw and said guiding sleeve about said adjust screw longitudinal axis, a fixing means for fixing said device to said thyroid cartilage with said guiding sleeve inserted in said window, said fixing means extending laterally from said sleeve base wall;

whereby a rotation of said adjustment screw causes said biasing block to slide inside said sleeve channel without causing said screw to move along said screw longitudinal axis relatively to said sleeve base wall.

9. A device as recited in claim 8 wherein said sleeve first aperture has a larger aperture segment that extends integrally into a radially contiguous smaller aperture segment, said larger aperture segment being configured and sized so as to allow through passage of said adjustment screw head, said smaller aperture segment being configured and sized so as to prevent the through passage of said adjustment screw head, whereby said adjustment screw spacing segment is adapted to extend through said smaller aperture segment of said sleeve first aperture with said adjustment screw head abuttingly contacting said sleeve base wall adjacent said smaller aperture segment so as to prevent a longitudinal axial displacement of said adjustment screw.

10. A vocal cord medializing device for medializing a vocal cord, said vocal cord being located inside a larynx, said larynx including a thyroid cartilage and a window formed in said thyroid cartilage adjacent said vocal cord, said device comprising:

a hollow guiding sleeve defining a sleeve channel, said sleeve channel extending between a sleeve proximal end and a sleeve distal end, said guiding sleeve being configured and sized so as to be insertable inside said window;

a sleeve base wall extending across said sleeve proximal end for closing the latter, a biasing block slidably inserted in said sleeve channel, said biasing block being movable between a retracted position wherein said biasing block is in a substantially proximal relationship relative to said sleeve base wall and a protracted position wherein said biasing block is in a substantially spaced relationship relative to said sleeve base wall;

an adjustment screw for moving said biasing block between said protracted and retracted positions, said adjustment screw being rotatably attached to said sleeve base wall and threadedly attached to said biasing block, said adjustment screw having a screw longitudinal axis;

a fixing means for fixing said device to said thyroid cartilage with said guiding sleeve inserted in said window, said fixing means extending laterally from said sleeve base wall;

whereby a rotation of said adjustment screw causes said biasing block to slide inside said sleeve channel without causing said screw to move along said screw longitudinal axis relative to said sleeve base wall, a sleeve second aperture, said sleeve second aperture being provided with a sleeve second aperture internal thread, said sleeve second aperture extending through said sleeve base wall;

a block second aperture extending through said biasing block, said block second aperture being positioned so as to be in a substantially coaxial relationship with said sleeve second aperture;

said block second aperture being configured so as to define an inwardly projecting second aperture abutment shoulder;

a stopper screw, said stopper screw having a stopper screw head, a stopper screw threaded segment and a non-threaded stopper screw spacing segment extending integrally between said stopper screw head and said stopper screw threaded segment, said stopper screw head being configured and sized so as to be slidably insertable into said block second aperture and so as to abut against said second aperture abutment shoulder, said stopper screw threaded segment being configured and sized so as to threadedly engage said sleeve second aperture internal thread, whereby said stopper screw head is adapted to slide inside and second block aperture when said biasing block is moved between said retracted position and said protracted position, said stopper screw head being adapted to abut against said second aperture abutment shoulder when said biasing block is in a fully protracted position so as to prevent further protraction of said biasing block.

11. A device as recited in claim 10 wherein said block second aperture has a second aperture larger segment, an integrally extending second aperture smaller segment and wherein said second aperture abutment shoulder is defined by the junction between said second aperture larger segment and said second aperture smaller segment.

12. A vocal cord medializing device for medializing a vocal cord, said vocal cord being located inside a larynx, said larynx including a thyroid cartilage and a window formed in said thyroid cartilage adjacent said vocal cord, said device comprising:

a hollow guiding sleeve defining a sleeve channel, said sleeve channel extending between a sleeve proximal end and a sleeve distal end, said guiding sleeve being configured and sized so as to be insertable inside said window;

a sleeve base wall extending across said sleeve proximal end for closing the latter wherein said sleeve base wall has a substantially rectangular and flat configuration defining a pair of transversely opposed base wall side peripheral edges and a pair of longitudinally opposed base wall end peripheral edges, said guiding sleeve including a pair of opposed sleeve side walls extending integrally and substantially perpendicularly from said base wall side peripheral edges and a pair of opposed sleeve end walls extending integrally and substantially perpendicularly from said base wall end peripheral edges, said sleeve side walls and said sleeve end walls merging integrally to form said sleeve channel, a biasing block slidably inserted in said sleeve channel, said biasing block being movable between a retracted position wherein said biasing block is in a substantially proximal relationship relative to said sleeve base wall and a protracted position wherein said biasing block is in a substantially spaced relationship relative to said sleeve basewall;

an adjustment screw for moving said biasing block between said protracted and retracted positions, said adjustment screw being rotatably attached to said sleeve base wall and threadedly attached to said biasing block, said adjustment screw having a screw longitudinal axis;

a fixing means for fixing said device to said thyroid cartilage with said guiding sleeve inserted in said window, said fixing means extending laterally from said sleeve base wall, said fixing means including a pair of substantially "Y"-shaped anchoring structures, said anchoring structures extending integrally and substantially outwardly from said opposed end peripheral edges of said sleeve base wall;

whereby a rotation of said adjustment screw causes said biasing block to slide inside said sleeve channel without causing said screw to move along said screw longitudinal axis relative to said sleeve base wall.

13. A device as recited in claim 12 wherein each of said anchoring structures includes a substantially annular-shaped main fixing ring and a pair of substantially annular-shaped auxiliary fixing rings, said auxiliary fixing rings being substantially symmetrically disposed relatively to said main fixing rings, said main fixing rings and said auxiliary fixing rings being adapted to receive a corresponding set of anchoring screws.

14. A device as recited in claim 13 wherein each of said main fixing ring is connected to an adjacent end peripheral edge by a main connecting member and wherein each of said auxiliary fixing rings is connected to an adjacent main fixing ring by corresponding auxiliary connecting members.

15. A device as recited in claim 14 wherein said main connecting members and said auxiliary connecting members are made of a substantially flat and thin bendable strip of material so as to allow said main fixing rings and said auxiliary fixing rings to be moved relatively to each other in various geometrical planes.

16. A device as recited in claim 15 wherein said main connecting members are positioned substantially aligned with said base wall longitudinal axis and wherein said auxiliary connecting members are positioned so as to form an angle having a value substantially in the range of forty degrees relatively to said base wall longitudinal axis.

17. A device as recited in claim 16 wherein said main fixing rings and said auxiliary fixing rings are each provided with an annular recess formed therein.

18. A device as recited in claim 17 wherein said anchoring structures have a thickness substantially in the range of 1.5 millimeters.

* * * * *